United States Patent [19]

Cauler et al.

[11] 4,207,288
[45] Jun. 10, 1980

[54] PHOTOINITIATOR SYSTEM FOR PHOTOPOLYMERIZABLE COMPOSITIONS

[75] Inventors: Caroline A. Cauler, Lancaster; Richard M. Fantazier, Columbia, both of Pa.

[73] Assignee: Armstrong Cork Company, Lancaster, Pa.

[21] Appl. No.: 895,258

[22] Filed: Apr. 10, 1978

Related U.S. Application Data

[62] Division of Ser. No. 699,711, Jun. 25, 1976, abandoned.

[51] Int. Cl.² .......................... G01K 7/00; G01N 25/20; G01N 33/00; B01J 31/02
[52] U.S. Cl. ...................................... 422/51; 73/190 R; 136/225; 136/230; 250/492 R; 252/426; 422/186
[58] Field of Search ................. 422/50, 51, 68, 186; 73/15 B, 190 R, 190 H; 250/492 R (U.S. only); 136/225

[56] References Cited

U.S. PATENT DOCUMENTS

| T947,004 | 6/1976 | Collins et al. .................. 422/186 X |
| 3,217,537 | 11/1965 | Hager, Jr. ........................ 73/190 R |
| 3,354,720 | 11/1967 | Hager, Jr. ........................ 73/359 X |
| 3,427,209 | 2/1969 | Hager, Jr. ........................ 73/190 H X |
| 3,767,470 | 10/1973 | Hines .............................. 73/190 H X |

OTHER PUBLICATIONS

ASTM Standards, Part 27 (Plastics–Methods of Testing), pp. 532–537, D1672–61T, Exposure of Polymeric Materials to High Energy Radiation, Jun. 1965.

*Primary Examiner*—Joseph Scovronek

[57] ABSTRACT

An apparatus for measuring an exothermic reaction in a thin film of a photopolymerizable, ethylenically-unsaturated mass, which apparatus comprises a thin foil differential thermocouple means, a pore means adjacent to and mounted above the thermocouple means, a perforated plate means positioned above the pore means and an ultraviolet light source means positioned above the plate means is disclosed.

2 Claims, 3 Drawing Figures

PHOTOINITIATOR SYSTEM FOR PHOTOPOLYMERIZABLE COMPOSITIONS

CROSS-REFERENCE TO RELATED APPLICATION

This is a division, of application Ser. No. 699,711, filed June 25, 1976, now abandoned.

BACKGROUND OF THE INVENTION

1. Field of the Invention

The present invention relates to an apparatus and method for the analysis of photopolymerization, a photopolymerization process and a photoinitiating composition. More particularly, it relates to an apparatus and method for photopolymerization analysis and a process for the photopolymerization of ethylenically-unsaturated organic compounds containing a photoinitiating system comprising a sensitizer of naphthalene or substituted naphthalene and an organic peroxygen-containing compound. It also relates to a photoinitiating composition comprising a peroxygen-containing naphthalenic compound.

2. Description of the Prior Art

The use of a variety of sensitizers in photochemical polymerization of monomers or mixtures of unsaturated polymers and monomers copolymerized with the latter is well known to those skilled in the art. Benzoin-derived sensitizers are among the most efficient for UV sensitive systems. For example, U.S. Pat. No. 2,448,828 describes the photopolymerization of a number of ethylenically-unsaturated compounds, such as acrylic and substituted acrylic acids, esters, amides, and nitriles, as well as vinyl and vinylidene compounds using benzoin $C_1$ to $C_3$ alkyl ethers as photoinitiators. The systems are noted to be activated at 180–700 millimicrons. Molding and coating compositions obtained from mixtures of unsaturated polyester resins and copolymerizable monomers have also been photopolymerized, as described in U.S. Pat. No. 3,502,487. Successful polymerizations occur at 250–500 millimicrons in the presence of certain benzoin aryl ethers. Other benzoin-derived photosensitizers are disclosed in U.S. Pat. Nos. 3,764,560; 3,814,702; and British Specification No. 1,156,460.

Historically, the use of photoinitiators such as the before-mentioned benzoin and its derivatives in photopolymerizable systems has been to facilitate the initiation of the polymerization reaction. Photoinitiators offer the advantage of enhanced curing speed at ambient conditions as opposed to conventionally-used thermal initiators, which require elevated temperatures for use. These thermal initiators are typically free-radical-generating sources whose function is to contribute catalytically to the polymerization reaction by enhancing the rate at which free-radical chains are initiated or by shortening the induction period for the reaction. The most acceptable of these free-radical-generating sources are those classified generally as peroxide initiators, including various organic peracids, peresters, percarbonates, peroxides and hydroperoxides, and azo initiators such as azoisobutyronitrile and the like. While desirable as initiators, these materials require that the polymerizable material in which they are incorporated be heated to an elevated temperature causing decomposition of the initiator, generating free radicals at a rate that will cause polymerization in a satisfactory period of time. For application on thermally-sensitive substrates, the use of thermal initiators may be undesirable. The use of thermal initiators that decompose to free-radical moieties at temperatures near ambient are also useful in polymerization reactions, but present a serious disadvantage in that the storage and shelf life of such composition is minimal.

In addition to the well-known benzoin initiators, haloalkyl-substituted naphthalenic derivatives have been disclosed as photochemical polymerization catalysts in U.S. Pat. No. 2,505,067.

While the above compounds are useful for the purpose for which they are intended, they have the above-mentioned limitations. In addition, many of the conventional photoinitiators bear chromophoric groups or form chromophoric groups during the course of polymerization that makes their use in uncolored, translucent or transparent resins disadvantageous. Further, many of the conventional photoinitiators are not effective as thermal polymerization initiators.

The analysis of thermally-polymerizing systems is a common practice among those skilled in the art of studying such polymerization processes, and methods and apparatus are available. In particular, thermal analyzers which measure exotherms of polymerizing systems are commonly used. The use of such methodology with photopolymerizing systems is severely restricted because of the requirements for supplying ultraviolet radiation to the sample in a manner that will both permit full light absorption and proper form, e.g. that the sample will duplicate conditions of actual use, specifically as a thin film in the case of coatings. In addition to the above problems, conventional thermal analyzers also require tedious manipulations to obtain a reproducible sample and do not respond satisfactorily to the very rapid polymerizations that are commonly encountered in the photopolymerization of thin-film coatings. These limitations prevent a completely reliable, accurate analysis of photopolymerizing systems.

SUMMARY OF THE INVENTION

It is one object of this invention to provide a photoinitiating polymerization process employing a composition that is active at ambient conditions.

It is a further object of this invention to provide a photoinitiating composition that is colorless and does not impart color to a photopolymerizable mass or photopolymerized product.

It is another object of this invention to provide a photoinitiating composition that is also a thermal initiating composition.

It is an additional object of the present invention to provide an apparatus for the measurement of photopolymerizing reactions.

It is a further object of this invention to provide a method for thermal analysis of photopolymerizing systems.

These and other objects of the present invention will be better understood from the following detailed description thereof, together with the accompanying drawing.

DESCRIPTION OF THE PREFERRED EMBODIMENTS

Figure 1:
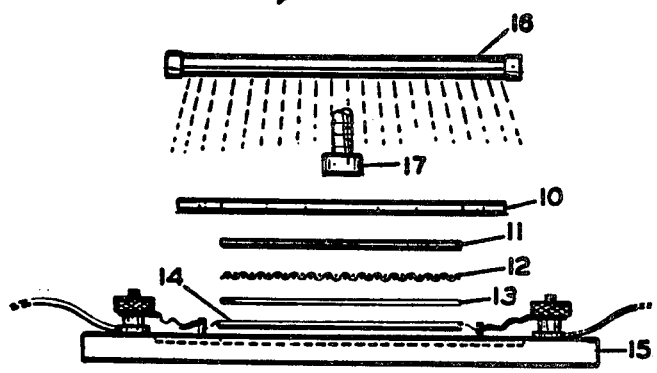
FIG. 1 is an exploded cross-sectional view of the thin film differential thermal analyzer.

In one embodiment of the present invention, the photoinitiating composition contains two essential ingredients. The first ingredient of this composition is an organic peroxygen-containing compound that is essentially responsible for supplying free radicals for the reaction of the photopolymerizing mass. The term peroxygen-containing compound includes any compound having the formula R'—O—O—R where R is aryoyl or alkyloyl and R' is hydrogen, aklyloyl, aryoyl, alkyl or aryl. Such compounds are illustrated by the acyl peroxides, hydroperoxides, ketone peroxides, peresters, peroxycarbamates and peroxy carbonates.

Any stable peroxide can be used in this composition. The term stable refers to peroxygen-containing compounds that do not auto-dissociate at or near room temperatures when stored in the absence of ultraviolet-containing light. It is only necessary that the peroxygen-containing compounds selected as the free radical source in the composition of this invention be capable of accepting electronic excitation energy from the photosensitizer and produce free radicals from the decay of the resulting excited state. Thus, for example, cyclic endoperoxides would not be acceptable free radical sources in these compositions. One of the unexpected aspects of this invention is that the free radical-generating, peroxygen-containing compounds can be selected from those that not only cleave by photochemical processes, but also those that had heretofore been thought to be only susceptible to thermal cleavage. This, therefore, permits a wide selection of photoinitiators as well as a variety of conditions to induce photoinitiation. Combined photo and thermal initiation is also readily accomplished. In this respect, the preferred peroxides used in these compositions are those known as high temperature curing peroxides and include the alkyl peroxycarbonates such as di-t-butyl peroxycarbonate and t-butyl peroxyisopropyl carbonate; the alkyl esters of aromatic and substituted aromatic peracids such as t-butyl perbenzoate and t-butyl-4-chloroperbenzoate, t-butyl-4-methoxy perbenzoate, t-butyl-4-methyl perbenzoate, 2,5-dimethylhexyl 2,5-di(peroxy benzoate), t-butyl 2-methylsulfonyl perbenzoate, and t-butyl 4-t-butyl-perbenzoate; and the alkyl esters of aromatic peroxy carbamates such as t-butyl-N-(2-chlorophenyl peroxy)carbamate, t-butyl-N-(2,5-dichlorophenyl peroxy)carbamate; and mixtures thereof. Other useful peroxygen-containing compounds include the alkyl or aryl peroxides, for example, dicumyl peroxide, benzoyl peroxide, lauroyl peroxide, methylethylketone peroxide and cyclohexanone peroxide.

The photochemical sensitizer useful as the second component in the photoinitiating compositions of this embodiment is naphthalene or its various derivatives. The naphthalenic photosensitizers preferred in the compositions of this invention are those that have absorption maxima in the 300 millimicron region of the electromagnetic spectra. Examples of the naphthalenic sensitizers suitable for use in the composition of this invention include naphthalene, $C_1$ to $C_8$ alkyl naphthalene, naphthaldehyde, naphthyl ketones, naphthyl esters of aromatic and aliphatic acids and mixtures of the compounds. Naphthalene itself has been found to be particularly suitable in this respect.

The photoinitiator composition of this invention containing the naphthalenic photosensitizer and the peroxygen-containing compound can be used in the photopolymerizable ethylenically-unsaturated mass in a concentration of from about 0.1 weight percent to about 20 weight percent based on the weight of photopolymerizable mass. It has been found advantageous to use from about 0.5–5 weight percent.

In cases where any of the components of the photoinitiator composition is a solid, it is preferable to dissolve such solid in the other component if such is a liquid. If both components are solids or they are not soluble in each other, then a photochemically inert solvent may be used. By photochemically inert is meant a solvent which will not absorb the photochemically produced energy resulting from photolysis in the polymerizing system. Such absorption of energy in photochemical systems is commonly referred to as quenching. Further, the solvent must not appreciably absorb the incident radiation, thereby preventing the photosensitizer from being activated (the process of excitation). In addition, the solvent must not appreciably retard the free-radical polymerization reaction. While any such solvent that does not quench excitation of the sensitizer or inhibit the polymerization reaction can be used, preferable are the non-aromatic hydrocarbon solvents such as hexane, aliphatic solvents such as acetonitrile, and the haloalkanes such as methylene chloride. To avoid processing problems, a minor amount of solvent should be used with respect to the photoinitiating composition such being only sufficient to dissolve the components, e.g., not over 50 weight percent solvent to photoinitiator composition.

The photoinitiator composition itself is active (photoinitiates) when used in the concentrations as disclosed above. The individual components of such concentrations is most effective when used in a ratio of 1:10 to 10:1 naphthalenic compound:peroxygen-containing compound. Particularly preferred is a ratio of 1:1.

In another embodiment in accordance with the present invention, it is possible to combine the naphthalenic sensitizer and the peroxygen initiator into a single compound to form a photoinitiator composition. Such combination is advantageously carried out by the following reaction sequence:

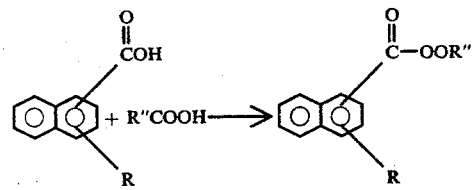

wherein R is as herein described and R" is an organic hydroperoxide of less than 15 carbon atoms per molecule selected from the group consisting of t-alkylhydroperoxide, secondary hydrocarbyl aralkyl hydroperoxide and tertiary hydrocarbyl aralkyl hydroperoxide. These compounds are well known in the prior art and, as indicated, are formed by the reaction between the respective naphthalene carboxylic acids and hydroperoxides, such being conducted in the presence of a catalytically sufficient amount of a strong acid; see for example U.S. Pat. No. 3,595,898. Alternately, the naphthalenic peroxide can be prepared by the reaction of the naphthalene acid halide with the alkali metal salt of the hydroperoxide as disclosed in J. Amer. Chem. Soc., 88, 3382 (1966).

The naphthalenic peroxygen-containing compounds can be used in photopolymerizable, ethylenically unsaturated compositions in concentrations of from about 0.1 to about 20 weight percent, preferably from 0.5–5 weight percent. As discussed earlier for the two-component system, when the naphthalenic peroxygen-containing compound is a solid, such is advantageously added to the photopolymerizable mass in the aforementioned photochemically inert solvent. Minor amounts of solvent should be used, such being only sufficient to dissolve the single component.

Figure 2:
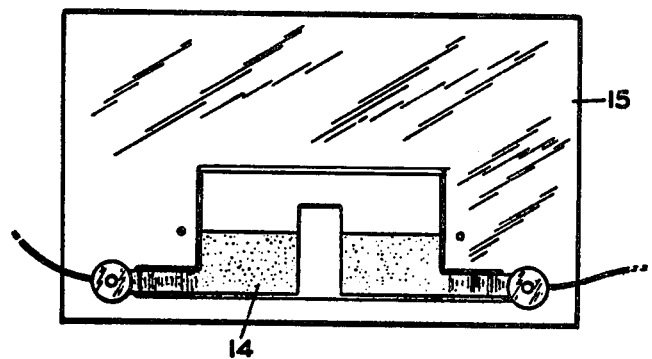
FIG. 2 is a top view of the analyzer only illustrating the thin foil thermocouple.
Figure 3:
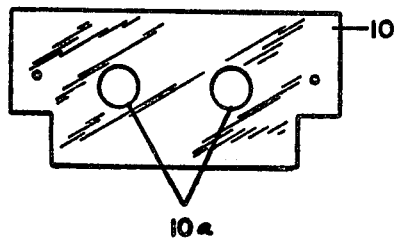
FIG. 3 is a top view of the perforated plate employed in the analyzer.

The ability of the photoinitiating composition of this invention to catalyze the photopolymerization of the ethylenically-unsaturated mass is determined by the method of thin film exothermic differential analysis, a further embodiment of this invention. A schematic representation of the instrument employed in this method is illustrated in FIGS. 1, 2 and 3. Referring to FIG. 1, which shows an exploded view of a thin film exothermic differential thermal analyzer, a conventional cover glass is used as a base plate 13 and is interposed between a photopolymerizable mass held in place by a thin, small pore component 12 and a thin foil thermocouple 14. The thin foil thermocouple 14 is from 0.0005 inch to 0.050 inch in thickness and is preferably copper constantan. Other thin foil thermocouple materials may be used such as iron constantan, chromium constantan, and the like. A copper constantan thermocouple of 0.002 inches in thickness is most preferred. Conventional cover glass, as used with microscopic slides and the like, have been found to be suitable for use in the base plate 13. The thin, small pore component 12 is advantageously a screen-like material of 8 to 10 mesh and has a thickness of from 0.002 to 0.010 inch. While any screen-like material can be employed that is inert to the components of the polymerizable mass, glass fiber scrim has been found to be most useful in this embodiment of over invention. For the maximum transmission of the proper wave lengths useful in initiating photopolymerization, a protective component 11 constructed from quartz is laid on top of the screen 12. This not only assures transmission of the ultraviolet wave lengths, but also keeps the photopolymerizing mass from contact with the perforated plate 10, which is opaque to ultraviolet light and is preferably aluminum. It also assures a uniform thickness of resin. The protective component 11 may be dispensed with if the perforated plate 10 is formed of a photopolymerizable inert material, such as opaque glass, and various opaque resins, such as polyethylene and phenolic resins. The entire assembly is clamped to a plate 15 with clamp 17. The support 15 is preferably formed of a phenolic resin, but the exact materials of construction of such support are not important. A UV light source 16 is employed to irradiate the sample exotherm cell, light passing through holes 10A (FIG. 3) in the perforated plate and contacting the photopolymerizable mass held in place by screen 12. As the photopolymerization is completed, any exothermic reaction is detected by the thin foil thermocouple 14. The electrical signal generated as a result of such exothermic response is passed into a conventional recording potentiometer. Such devices are well known in the prior art as useful for measuring small electrical outputs (millivolts and the like) from thermocouple-generated signals.

In order that this invention may still more readily be understood, the following detailed working examples are given by way of illustration only:

Peresters useful in accordance with the present invention are readily prepared by the addition of an acid chloride to a mixture of the alkali metal salt of t-butyl hydroperoxide. Example 1, while specifically disclosing the synthesis of the one component photoinitiator composition in accordance with the present invention, should also be regarded as a synthesis of general applicability for the preparation of peroxygen-containing compounds.

EXAMPLE 1

A. Sodium t-Butyl Hydroperoxide

To a stirred suspension of 2.28 g (0.095 mol) of sodium hydride (from 4.56 g of a 50% dispersion in mineral oil) in 200 ml of dry diethyl ether at 0° C. was added slowly 10 g (0.11 mol) of t-butyl hydroperoxide, and the resulting reaction mixture stirred for a period of 15 hours while maintaining its temperature below 15° C. The sodium t-butyl hydroperoxide was removed by filtration, washed with ether, air dried and stored in a desiccator at 0° C.

B. t-Butyl Pernaphthoate

To a stirred slurry of 2.80 g (0.025 mol) of sodium t-butyl hydroperoxide in 100 ml of methylene chloride at 0° C. was added dropwise over 35 minutes a solution of 3.81 g (0.020 mol) of 1-naphthoyl chloride. After stirring for one hour, the reaction mixture was allowed to stand at 0° C. overnight. The mixture was then suction filtered to remove sodium chloride (1.13 g was recovered). The filtrate containing the crude product was dried over magnesium sulfate, filtered, and the solvent removed in vacuo at ambient temperature to yield 4.77 g of t-butyl pernaphthoate as a pale straw colored oil. Its infrared spectrum was essentially free of hydroxyl absorption and the product exhibits a strong carbonyl absorption at 1750 $cm^{-1}$. Iodometric analysis indicated 95% peroxide.

EXAMPLE 2

To 10.0 g of tetraethyleneglycol diacrylate was added 0.100 g of t-butyl perbenzoate and 0.100 g of naphthalene and the resulting composition stirred to form a homogeneous solution. A portion of the resulting composition was placed in a watch glass and its surface was covered with a polyethylene film, 0.001" thick, to exclude air. The sample was exposed to the radiation from a 450 watt medium-pressure mercury arc (Hanovia, Inc.) at a distance of 3 inches for two minutes, during which time the composition polymerized to a solid mass. In an identical experiment, a sample of tetraethyleneglycol diacrylate containing no photoinitiator failed to polymerize.

EXAMPLE 3

A composition was prepared consisting of tetraethyleneglycol diacrylate containing 2-ethylhexyl acrylate as a diluent. The resulting composition was not polymerized after exposure to the 450 watt mercury arc lamp of Example 1 for a period of 4 minutes. An identical sample was formulated containing 1% by weight each of t-butyl perbenzoate and naphthalene. This latter composition polymerized to a solid mass during a 2-minute exposure time.

EXAMPLE 4

To a 10.0 gram sample of tetraethyleneglycol diacrylate (TEGDA) was added 0.5% of t-butyl pernaphthoate and the resulting composition mixed with a mechanical stirrer to form a homogeneous mixture. A glass fiber scrim was saturated with this mixture and placed in the thin film exothermic differential analyzer, as described above. The apparatus was then exposed to the radiation from a 450 watt medium-pressure mercury arc at a distance of 3 inches. The curing of the liquid film caused an exotherm (within two minutes) of 2.35° C.

EXAMPLE 5

Example 4 was repeated using 1.0% of t-butyl pernaphthoate to the TEGDA. An exotherm of 2.40° C. was recorded.

The following examples demonstrate the efficiency of a variety of combinations of the photoinitiator composition of this invention using the thin foil differential exothermic analyzer heretofore disclosed. Typically, a small sample (about 0.1 ml) of the photopolymerizable ethylenically-unsaturated liquid is placed on the screen 12 (FIG. 1). Only enough sample is placed on said screen so that an area somewhat greater than the area exposed to UV irradiation through the mask 10 is occupied. Nujol, or some equivalent mineral oil, is placed next to the sample so that its area, similar to the photopolymerizable composition, is somewhat greater than holes 10A in the perforated plate (FIG. 2). As viewed from above, one side of such plate then contains the photopolymerizable mass, the other side, the mineral oil. The cell is assembled as shown in FIG. 1 and the stack clamped together. Thermocouple leads are attached to any conventional recorder capable of measuring electromotive forces from thermocouple sources. The sample is irradiated with ultraviolet light from light source 16 and the exotherm generated from the reaction recorded as the response of the differential thermocouple as a function of irradiation time.

The two-component photoinitiating composition in accordance with the present invention utilizes a wide variety of peroxygen-containing compounds as well as naphthalenic compounds. Table I illustrates examples representative of the former and Table II, examples representative of the latter.

Table I

| Example | Photoinitiator[a] | Photopolymerizable Mass | Exotherm[b] (Relative) |
| --- | --- | --- | --- |
| Comparative | t-butyl perbenzoate | TEGDA | 1.00 |
| Comparative | cumene hydroperoxide | " | 0.08 |
| Comparative | lauroyl peroxide | " | 0.84 |
| Comparative | t-butyl hydroperoxide | " | 0.04 |
| Comparative | naphthalene | " | 0.30 |
| 6 | t-butyl perbenzoate + naphthalene | " | 1.68 |
| 7 | cumene hydroperoxide + naphthalene | " | 0.32 |
| 8 | lauroyl peroxide + naphthalene | " | 1.32 |
| 9 | t-butyl hydroperoxide + naphthalene | " | 0.68 |

[a] All photoinitiator components are 1% by weight of photopolymerizable mass.
[b] All exotherms are recorded relative to the arbitrary standard t-butyl perbenzoate. This compound, when added to the photopolymerizable mass and exposed to UV light (see Example 1), resulted in a polymerization exotherm of 0.25° C.

Table II

| Example | Photoinitiator[a] | Photopolymerizable Mass | Exotherm[a] (Relative) |
| --- | --- | --- | --- |
| Comparative | 1-methyl naphthalene | TEGDA | 0.04 |
| Comparative | naphthaldehyde | " | 1.28 |
| Comparative | 1-bromonaphthalene | " | 1.92 |
| Comparative | naphthyl phenyl ketone | " | 0.08 |
| Comparative | t-butyl perbenzoate 1-bromonaphthalene | " | 2.32 |
| Comparative | lauroyl peroxide 1-bromonaphthalene | " | 2.60 |
| Comparative | cumene hydroperoxide 1-bromonaphthalene | " | 1.60 |
| 10 | t-butyl perbenzoate naphthyl phenyl ketone | " | 1.12 |
| 11 | lauroyl peroxide naphthyl phenyl ketone | " | 1.68 |
| 12 | t-butyl perobenzoate 1-naphthaldehyde | " | 1.52 |
| 13 | lauroyl peroxide 1-naphthaldehyde | " | 2.40 |
| 14 | cumene hydroperoxide 1-naphthaldehyde | " | 1.88 |
| 15 | t-butyl perbenzoate acetonaphthone | " | 1.64 |
| 16 | t-butyl perbenzoate 1-methyl naphthalene | " | 0.68 |

[a] See Table I

Table II particularly discloses that the two-component composition cannot be simply selected from any naphthalenic compound. The 1-bromonaphthalene composition exhibits a disadvantageous negative synergism.

Table III

| Example | Photoinitiator[a] | Photopolymerizable Mass | Exotherm (Relative) |
| --- | --- | --- | --- |
| Comparative | t-butyl perbenzoate | Acrylate terminated urethane of molecular weigt 10,000–20,000 and containing 40–50% monomeric acrylate | 0 |
| Comparative | naphthalene | Acrylate terminated urethane of molecular weight 10,000–20,000 and containing 40–50% monomeric acrylate | 0 |
| 17 | t-butyl perbenzoate naphthalene | Acrylate terminated urethane of molecular weight 10,000–20,000 and containing 40–50% monomeric acrylate | 0.04 |
| 18 | t-butyl perbenzoate naphthyl phenyl ketone | Acrylate terminated urethane of molecular weight 10,000–20,000 and containing 40–50% | 0.20 |

Table III-continued

| Example | Photoinitiator[a] | Photopolymerizable Mass | Exotherm (Relative) |
|---|---|---|---|
| Comparative | t-butyl perbenzoate 1-bromonaphthalene | monomeric acrylate Acrylate terminated urethane of molecular weight 10,000–20,000 and containing 40–50% monomeric acrylate | 0.36 |
| Comparative | t-butyl perbenzoate | ENE-Thiol[b] | 1.00 |
| Comparative | naphthalene | ENE-Thiol[b] | 0.30 |
| 19 | t-butyl perbenzoate naphthalene | ENE-Thiol[b] | 1.45 |
| 20 | t-butyl perbenzoate naphthalene | ENE-Thiol[b] | 1.31 |
|  | t-butyl perbenzoate naphthalene | ENE-Thiol[b] | 1.06 |

[a]Photoinitiator concentrations are 1% unless otherwise exemplified.
[b]Photopolymerizable composition of U. S. Pat. 3,661,744, Example 106.

As disclosed earlier and as pointed out above, benzoin-like materials have, in many cases, been found to be photoinitiators in themselves, as well as photosensitizers when used in conjunction with free radical sources. In the compositions of this invention, the use of benzoin derivatives shows equal or increased activity over those compositions not incorporating such benzoin materials, but advantageously conferring sensitivity to heat as well. The following table discloses this synergism in more detail.

Table IV

| Example[a] | Initiator | Relative Exotherm of Polymerization |
|---|---|---|
| Comparative | Benzoin + Naphthalene | 1.00 |
| Comparative | 4,4'-dimethylbenzophenone (DMBP) + naphthalene | 0.90 |
| Comparative | 2,2-diethoxybenzophenone (DEAP) + naphthalene | 1.19 |
| 21 | Benzoin + Naphthalene + t-BPB | 1.55 |
| 22 | DMPB + Naphthalene + t-BPB | 1.93 |
| 23 | DEAP + Naphthalene + t-BPB | 1.46 |

[a]All photopolymerizable compositions were tetraethylene glycol diacrylate. All initiator components were used at a level of 1% by weight of such photopolymerizable mass.

What is claimed is:

1. An apparatus for measuring an exothermic reaction in a photopolymerizable, ethylenically-unsaturated mass which apparatus comprises:
   (a) a thin foil differential thermocouple means;
   a thin, small pore means capable of retaining said photopolymerizable, ethylenically-unsaturated mass adjacent to and mounted above said thermocouple means;
   (c) a perforated plate means opaque to ultraviolet light positioned above said small pore means; and
   (d) an ultraviolet light source means positioned above said plate means, said above four means being positioned one above to other to permit the ultraviolet light source means to pass ultraviolet light rays through said perforated plate means and irradiate said mass mounted on said pore means.

2. The apparatus of claim 1 wherein said thin foil differential thermocouple is from 0.0005 to 0.050 inch in thickness and said thin, small pore means is screen of 8 to 10 mesh and from 0.002 to 0.010 inch in thickness.

UNITED STATES PATENT AND TRADEMARK OFFICE
Certificate

Patent No. 4,207,288                                                      Patented June 10, 1980

Caroline A. Cauler and Richard M. Fantazier

Application having been made by Caroline A. Cauler and Richard M. Fantazier, the inventors named in the patent above identified, for the issuance of a certificate under the provisions of Title 35, Section 256, of the United States Code, deleting the name of Caroline A. Cauler as a joint inventor, and a showing and proof of facts satisfying the requirements of the said section having been submitted, it is this 4th day of November 1980, certified that the name of the said Caroline A. Cauler is hereby deleted from the said patent as a joint inventor with the said Richard M. Fantazier.

FRED W. SHERLING,
*Associate Solicitor.*